United States Patent [19]
Lekhtman et al.

[11] Patent Number: 5,333,618
[45] Date of Patent: Aug. 2, 1994

[54] PORTABLE SELF-CONTAINED INSTRUMENT FOR THE MEASUREMENT OF NERVE RESISTANCE OF A PATIENT

[76] Inventors: Gregory Lekhtman, 1550 Dr. Penfield Ave., Apt. PH.3, Montreal, Quebec, Canada, H3G 1B6; Roy Stephan, 3550 Ridgewood, Apt. 40, Montreal, Quebec, Canada, H3V 1C2

[21] Appl. No.: 85,585

[22] Filed: Jun. 30, 1993

[51] Int. Cl.⁵ .............................................. A61B 5/05
[52] U.S. Cl. .................................. 128/734; 128/741
[58] Field of Search ............... 128/734, 741, 733, 774, 128/782

[56] References Cited

U.S. PATENT DOCUMENTS 4,807,643  2/1989  Rosier ................................. 128/741
5,215,100  1/1993  Spitz et al. ........................ 128/741

Primary Examiner—Angela D. Sykes
Attorney, Agent, or Firm—Chilton, Alix & Van Kirk

[57] ABSTRACT

The instrument consists of a hollow elongated cylindrical housing having a stimulator circuit and a receptor circuit disposed therein. Stimulator leads are connected to the stimulator circuit and receptor leads are connected to the receptor circuit. The housing includes a display means and a stimulator circuit activator switch. The stimulator leads are connected to stimulator electrodes mounted at a first position on the patient, and the receptor leads are connected to receptor electrodes mounted at a second position on the patient. The first position is spaced from the second position and the first and second positions are disposed along the path of a nerve of the patient. The suspected damaged portion of the nerve is between the first and second positions. The stimulator circuit activator switch is activated so that a stimulator pulse is applied, via the stimulator leads and the stimulator electrodes, to the nerve at the first position. This pulse is transmitted along the nerve from the first position to the second position, and is received at the second position by the receptor circuit, via the receptor electrodes and the receptor leads. The time of travel of the pulse from the first position to the second position is measured and displayed on the display to provide a measure of the resistance of the nerve.

7 Claims, 2 Drawing Sheets

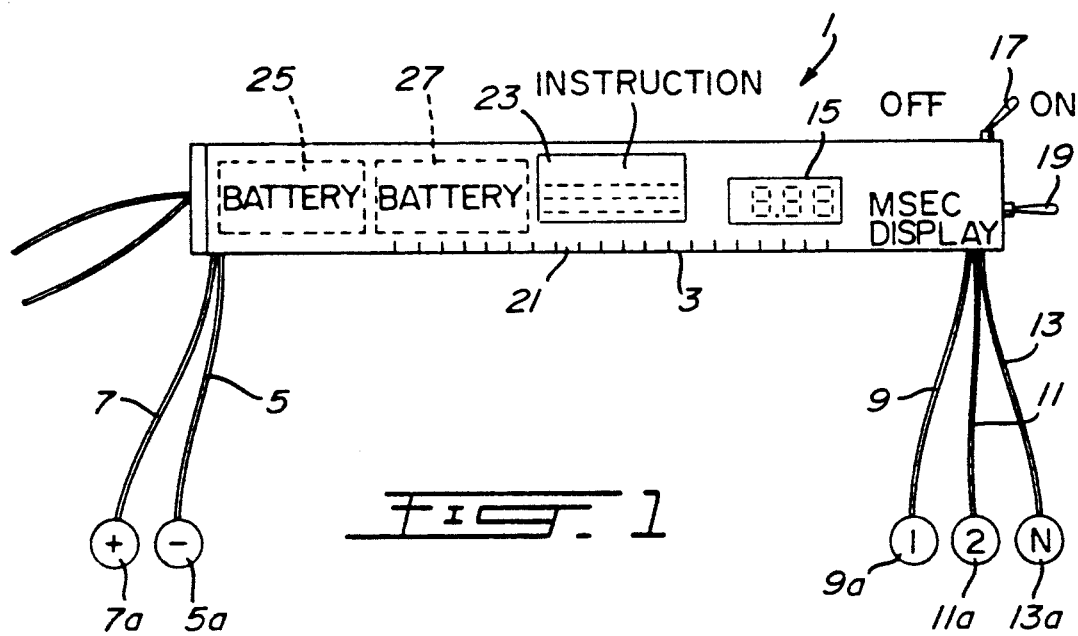
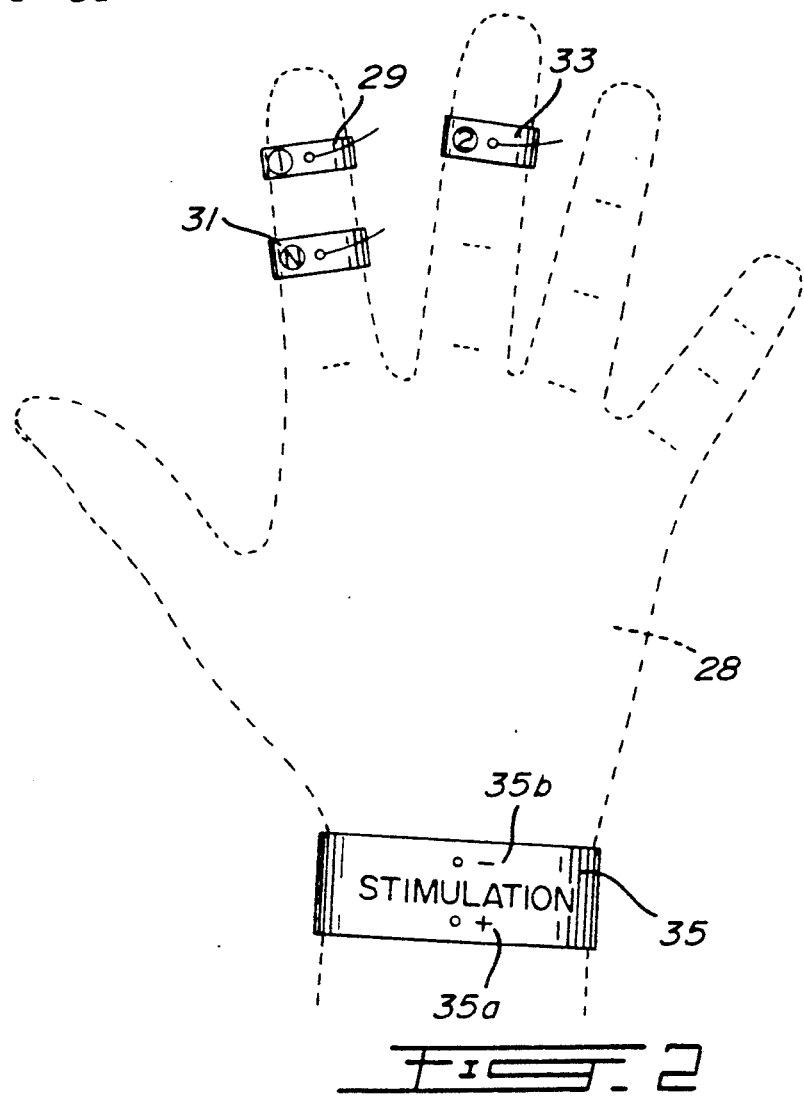

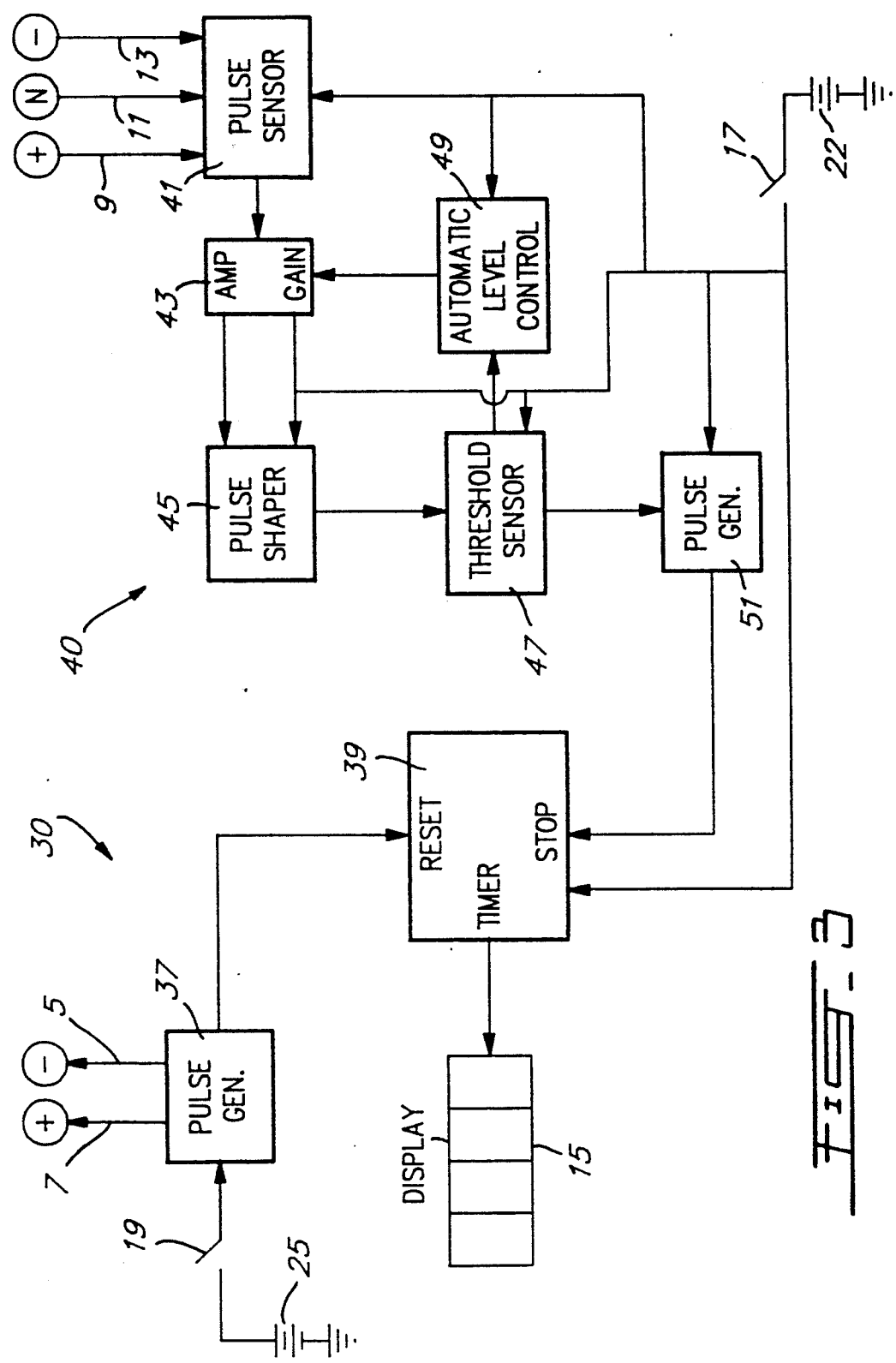

000# PORTABLE SELF-CONTAINED INSTRUMENT FOR THE MEASUREMENT OF NERVE RESISTANCE OF A PATIENT

BACKGROUND OF INVENTION

1. Field of the Invention

The invention relates to an instrument for the measurement of nerve resistance of a patient. More specifically, the invention relates to a portable, self-contained such instrument, which provides instant results.

2. Description of Prior Art

Instruments for the measurement of nerve resistance are already known in the prior art. However, typically, presently available instruments are large and not normally placed in an operating theater. In addition, the instruments require specialized training for their use and operation. As a result, procedures for correcting faulty nerves take much longer to complete and are more expensive than they need be.

In a typical present-day scenario, a doctor first examines the patient after which he may believe that there are nerve problems. The doctor will then send this patient to a facility having an instrument for measuring the resistance of the nerve. Tests are taken, and the results of the tests have to be analyzed before the examining physician can receive information concerning the state of the patient's nerves. Up to now, a considerable amount of time has passed between the time the physician saw the patient and the time at which the physician receives the information.

If the physician's suspicions are confirmed, and the physician considers that corrective surgery must be performed, then the surgery has to be scheduled and performed. As there is no instrument in the operating theater, the patient again has to be sent to a facility including such an instrument where tests are again taken. There will, of course, be a certain passage of time between the decision to schedule tests, and the date at which an appointment can be had. The results are once again analyzed and submitted to the examining physician. Only at that point, which would be months after an original examination, would the physician be aware of whether or not the corrective surgery was successful. If it was not successful, then further surgery has to be scheduled, further tests taken and so forth. This is obviously an unsatisfactory state of affairs.

SUMMARY OF INVENTION

It is therefore an object of the invention to provide an instrument for the measurement of nerve resistance of a patient which overcomes the disadvantages of the prior art such instruments.

It is a more specific object of the invention to provide a portable, self-contained such instrument which provides instant results.

It is an even more specific object of the invention to provide such an instrument which can be taken into and used in the operating theater as well as in other locations.

In accordance with a particular embodiment of the invention there is provided a portable, self-contained instrument for the measurement of nerve resistance of a patient, comprising:

a hollow elongated housing;
stimulator circuit means disposed in said housing;
receptor circuit means disposed in said housing;
stimulator connection means, connected to said stimulator circuit means, extending from said housing;
receptor connection means, connected to said receptor circuit means, extending from said housing;
display means; and
stimulator circuit activator means;

wherein, when said stimulator connection means are connected to stimulator electrodes mounted at a first position on said patient, and said receptor connection means are connected to receptor electrodes, mounted at a second position on said patient, said first position being spaced from said second position, each said first and second positions being disposed on a nerve of said patient, a suspected damaged portion of said nerve being between said first and second positions, and said stimulator circuit activator means is activated, a stimulator pulse is applied, via said stimulator connection means and said stimulator electrodes, to said nerve at said first position, and is transmitted along said nerve from said first position to said second position, and is received at said second position by said receptor circuit, via said receptor electrodes and said receptor connector means, the time of travel of said pulse from said first position to said second position being measured and displayed on said display to provide a measure of the resistance of said nerve.

BRIEF DESCRIPTION OF DRAWINGS

The invention will be better understood by an examination of the following description, together with the accompanying drawings, in which:

FIG. 1 illustrates one embodiment of an instrument in accordance with the invention;

FIG. 2 illustrates the placement of electrodes on a portion of the patient's body; and FIG. 3 is a block diagram of the electronic circuits forming a part of the instrument.

DESCRIPTION OF PREFERRED EMBODIMENTS

Referring to FIG. 1, an instrument in accordance with the invention, indicated generally at 1, comprises a hollow, elongated housing 3. Although the housing 3 could be square or rectangular or any other shape in cross-section, in accordance with a preferred embodiment, the housing 3 comprises an elongated cylinder.

Extending from the housing 3 are stimulator leads 5 and 7. Also extending from the housing 3 are receptor leads 9, 11 and 13. Preferably, the stimulator leads 5 and 7 are at one end of the housing 3 and the receptor leads 9, 11 and 13 are at the other end thereof.

The housing 3 also includes a display 15 which is, for example, a LCD display. The circuitry is adjusted so that the read-out on the display 15 is in msec.

The instrument also includes an ON-OFF switch 17 and a simulator circuit activator switch 19. The purpose and function of these switches will be described below.

Inscribed on the outer surface of the housing 3 is a scale 21 in either inches or centimeters. Also inscribed on the outer surface of the housing 3 is a list of instructions 23. As will be seen below with regards to FIG. 3, the housing 3 houses two separate batteries 25 and 27. The batteries are preferably 9-volt alkaline batteries.

FIG. 2 illustrates how electrodes are mounted on a portion of the body of a patient to receive the ends 5a, 7a, 9a, 11a and 13a of leads 5, 7, 9, 11 and 13 respectively. As can be seen, receptor electrodes 29, 31 and 33 will receive the ends 9a, 13a and 11a of the leads 9, 13 and 11 respectively. In FIG. 2, the electrodes are illustrated as being carried on bands. Any form of electrodes, either disposable or non-disposable, can be used for this purpose.

Spaced from the receptor electrodes 29, 31 and 33 are stimulator electrodes 35a and 35b mounted on a band 35. Once again, any well known electrodes, either disposable or non-disposable, can be used in this place. The ends 5a and 7a of the leads 5 and 7 are connected to electrodes 35b and 35a respectively.

The electrodes will be placed along the path of a nerve which is believed to be damaged in such a way that the damaged portion of the nerves will be between the stimulator electrodes 35a and 35b and the receptor electrodes 29, 31 and 33. Although in FIG. 2 the portion 28 of the patient's body is a hand, obviously, the portion could be any other portion of the patient's body along which a nerve path extends.

Turning now to FIG. 3, there is illustrated a stimulator circuit, illustrated generally at 30, and a receptor circuit, illustrated generally at 40. The stimulator circuit 30 comprises one of the batteries 25, the stimulator circuit activator switch 19, and a pulse generator 37. As can be seen, leads 5 and 7 are connected to the pulse generator 37 so that a pulse generated by the pulse is carried by these leads to respective electrodes to thereby stimulate the nerve of interest.

The receptor's circuit comprises a pulse sensor 41 to which are connected leads 9, 11 and 13. The output of the pulse sensor 41 is fed to a variable gain amplifier 43, and the output of the amplifier 43 is fed to a pulse shaper 45. The input of threshold sensor 47 is connected to the output of pulse shaper 45, and the output of the threshold sensor 47 is connected to an automatic level control 49 whose output is connected to a gain control terminal of the amplifier 43. The output of the threshold sensor 47 is then connected to a second pulse generator 51.

Also included with the circuitry is a timer 39. The output of pulse generator 37 is fed to the RESET terminal of the timer 39, and the output of the pulse generator 51 is fed to the STOP terminal of the timer 39. The output of the timer 39 is fed to the display 15, and the output of the timer drives the display.

As also seen in FIG. 3, when ON-OFF switch 17 is closed, power from battery 27 is provided to all of the elements of the receptor circuitry and to the timer 39.

In operation, electrodes 35a and 35b are mounted on a patient's body along the path which a nerve of interest travels. Mounted along the same path, but spaced from the electrodes 35a and 35b, are electrodes 29, 31 and 33. The suspected damaged portion of the nerve is, as above-mentioned, between the sets of electrodes. The distance between the stimulator electrodes 35a and 35b and the receptor electrodes 29, 31 and 33 is measured using the scale 21 on the housing 3. In this regard, one end of the scale is placed midway between the electrodes 35a and 35b, and the other end of the scale is placed at the position of the electrode 29. Leads 5 and 7 are connected to electrodes 35b and 35a respectively, while leads 9, 11 and 13 are connected to electrodes 29, 33 and 31 respectively. The ON-OFF switch 17 is turned ON, and the stimulator circuit activation switch 19 is activated. When switch 19 is activated, pulse generator 37 initiates a pulse which is transmitted, via leads 5 and 7, and electrodes 35b and 35a, to the nerve of interest. At the same time, the pulse generator 37 sends a pulse to the RESET terminal of the timer 39 to start the timer counting and to set the LCD display 15 to zero.

The pulse is transmitted along the nerve under observation and, when it reaches the electrode 29, the pulse sensor 41 is activated. The output of the pulse sensor is amplified and shaped and subsequently transmitted to the STOP terminal of the timer 39. At that time, the timer 39 no longer drives the display 15 so that the number on the display 15 indicates the passage of time for the travel of the pulse along the nerve between the stimulator electrode and the receptor electrode. As mentioned, the time on the display will be given in milliseconds.

If desired, the speed of the travel can be calculated by simply dividing the number on the display by the distance between the stimulator and the receptor electrodes. This distance should be given in centimeters so that the speed will be given in msec/cm.

The automatic level control measures the level of noise and the level of response and sets up appropriate levels for the signal to trigger the timing circuitry. Such control means are well known in the art and require no further description.

The unit is operated by two batteries as, if one single battery was used for both the stimulator 30 circuit and the receptor circuit 40, there could be interference between the two circuits to give false results. In this regard, the output of the pulse sensor is of the level of microvolts whereas the stimulator pulse generator 37 provides an output of over 100 volts.

With the inventive instrument, which, as above mentioned, can be used in the operating room, the surgeon can conduct a test even while the nerve of the patient is still exposed so that he can immediately determine the success or otherwise of the operation. Obviously, if the operation is not successful, then corrective measures can be taken right at that moment.

Thus, it can be seen that the instrument reduces greatly the expenditure of both time and money.

Although a particular embodiment has been described, this was for the purpose of illustrating, but not limiting, the invention. Various modifications, which will come readily to the mind of one skilled in the art, are within the scope of the invention as defined in the appended claims.

We claim:

1. A portable, self-contained instrument for the measurement of nerve resistance of a patient, comprising:
a hollow elongated housing;
stimulator circuit means disposed in said housing;
receptor circuit means disposed in said housing;
stimulator connection means, connected to said stimulator circuit means, extending from said housing;
receptor connection means, connected to said receptor circuit means, extending from said housing;
display means; and
stimulator circuit activator means;
wherein, when said stimulator connection means are connected to stimulator electrodes mounted at a first position on said patient, and said receptor connection means are connected to receptor electrodes, mounted at a second position on said patient, said first position being spaced from said second position, each said first and second positions being disposed on a nerve of said patient, a suspected damaged portion of said nerve being between said first and second positions, and said stimulator circuit activator means is activated, a stimulator pulse is applied, via said stimulator connection means and said stimulator electrodes, to said nerve at said first position, and is transmitted along said nerve from said first position to said second position, and is received at said second position by said receptor circuit, via said receptor electrodes and said receptor connector means, the time of travel of said pulse from said first position to said second position being measured and displayed on said display means to provide a measure of the resistance of said nerve;

wherein said stimulator connection means comprise a first conductive stimulator lead for connection to a positive stimulator electrode and a second conductive stimulator lead for connection to a negative stimulator electrode;

and wherein said receptor connection means comprise a first conductive receptor lead for connections to a positive receptor electrode, a second conductive receptor lead for connection to a negative receptor electrode and a third conductive receptor lead for connection to a neutral receptor electrode;

and wherein said stimulator circuit means comprises a pulse generator having first output means connected to said conductive stimulator leads, and second output means;

and including a first battery providing power to said pulse generator;

said stimulator circuit activation means comprising a switch connecting said first battery to said stimulator circuit means;

and wherein said receptor circuit means comprises a pulse sensor arrangement having first output means connected to said conductive receptor leads and second output means;

and further including a second battery providing power to said pulse sensor arrangement.

2. An instrument as defined in claim 1 and further including a timer circuit having a RESET input and a STOP input;

said second output means of said pulse generator being connected to said RESET input;

said second output means of said pulse sensor arrangement being connected to said STOP input;

said timer measuring the time elapsed between the onset of a stimulator pulse by said pulse generator and the reception of said pulse by said pulse sensor arrangement.

3. An instrument as defined in claim 2 wherein said pulse sensor arrangement includes level control means.

4. An instrument as defined in claim 3 wherein said electrodes are disposable.

5. An instrument as defined in claim 4 wherein said elongated surface has measuring means inscribed on the outer surface thereof.

6. An instrument as defined in claim 5 wherein the elongated housing has instructions inscribed on the outer surface thereof.

7. An instrument as defined in claim 6 wherein said hollow elongated housing comprises an elongated cylinder.

* * * * *